(12) United States Patent
Kimura et al.

(10) Patent No.: US 6,743,363 B2
(45) Date of Patent: Jun. 1, 2004

(54) METHOD OF BACTERIOSTASIS OR DISINFECTION FOR PERMSELECTIVE MEMBRANE

(75) Inventors: Takuhei Kimura, Otsu (JP); Yuichiro Nakaoki, Otsu (JP); Yohito Ito, Kyoto (JP); Yoshinari Fusaoka, Yokaichi (JP); Toshihiro Miyoshi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 38 days.

(21) Appl. No.: 10/230,129

(22) Filed: Aug. 29, 2002

(65) Prior Publication Data

US 2003/0080058 A1 May 1, 2003

Related U.S. Application Data

(62) Division of application No. 09/508,886, filed as application No. PCT/JP99/03860 on Jul. 16, 1999, now Pat. No. 6,468,430.

(30) Foreign Application Priority Data

Jul. 21, 1998 (JP) ............................. 10-204873
Apr. 13, 1999 (JP) ............................. 11-104985

(51) Int. Cl.$^7$ .............................................. B01D 65/02
(52) U.S. Cl. ........................ 210/636; 210/137; 210/199; 210/321.69; 210/639; 210/652; 210/764; 210/806
(58) Field of Search ................................ 210/137, 199, 210/202, 259, 321.69, 636, 639, 650–653, 702, 743, 764, 806; 422/28

(56) References Cited

U.S. PATENT DOCUMENTS

| | | | |
|---|---|---|---|
| 3,827,976 A | 8/1974 | Stana et al. | 210/636 |
| 3,850,797 A | 11/1974 | Lyatt | 210/23 |
| 4,169,789 A | 10/1979 | Lerat | 210/652 |
| 4,574,049 A | 3/1986 | Pittner | 210/639 |
| 5,460,723 A | * 10/1995 | Bourbigot et al. | 210/639 |
| 5,501,798 A | * 3/1996 | Al-Samadi et al. | 210/652 |
| 5,888,401 A | 3/1999 | Nguyen | 210/650 |
| 6,303,037 B1 | * 10/2001 | Tamura et al. | 210/652 |

FOREIGN PATENT DOCUMENTS

| | | |
|---|---|---|
| EP | 0 082 705 | 6/1983 |
| JP | 52-49645 | 4/1977 |
| JP | 55-129107 | 10/1980 |
| JP | 55-162309 | 12/1980 |
| JP | 58-109182 | 7/1983 |
| JP | 62-176507 | 8/1987 |
| JP | 1-135506 | 5/1989 |
| JP | 1-307407 | 12/1989 |
| JP | 2.265.628 | 10/1990 |
| JP | 8-71556 | 3/1996 |
| JP | 9-29075 | 2/1997 |
| JP | 11-9973 | 1/1999 |
| WO | 98 22205 | 5/1998 |

OTHER PUBLICATIONS

Reverse Osmosis and Ultrafiltration II. Application Membrane Technology Handbook. Jun 30, 1978. Haruhiko Oya et al. Hiroshi Harada. Saiwai Shobo Co., Ltd.. 3058–0055–2707.

Derwent Abstract Accession No. 65911X 35. Class D15. J51081789 (I BARA INHLCO KK). 1976.

* cited by examiner

*Primary Examiner*—Joseph Drodge
(74) *Attorney, Agent, or Firm*—Morrison & Foerster LLP

(57) ABSTRACT

In the invention, the pipe lines around permselective membranes and the surfaces of permselective membranes are intermittently disinfected by adding an inexpensive acid such as sulfuric acid or the like to pre-treated crude water so as to make the water have a pH of 4 or lower. Accordingly, the invention provides a method of surely disinfecting the permselective membranes in membrane separation systems.

11 Claims, 1 Drawing Sheet

METHOD OF BACTERIOSTASIS OR DISINFECTION FOR PERMSELECTIVE MEMBRANE

This application is a divisional of U.S. patent application Ser. No. 09/508,886, filed on Mar. 20, 2000, now U.S. Pat. No. 6,468,430, which is a 371 of PCT/JP99/03860, filed Jul. 16, 1999, and claims the benefit of Japanese applications 204873/98 filed Jul. 21, 1998 and 104985/99 filed Apr. 13, 1999.

TECHNICAL FIELD

The present invention relates to a method for pre-treatment of crude water in membrane separation, especially for that in reverse osmosis for desalination or separation, for example, in reverse osmosis for desalination of seawater, to a method of bacteriostasis or disinfection for membranes, and to an apparatus for them.

BACKGROUND OF THE INVENTION

Membrane separation is much used in various fields of desalination of seawater and saltwater, production of pure water and ultrapure water for medical and industrial use, treatment of industrial drainage, etc. In such membrane separation, contamination of the membrane separation apparatus with microorganisms worsens the quality of permeates and lowers the membrane permeability and separability owing to the growth of microorganisms on and around the membranes or to the adhesion of microorganisms and their metabolites onto them. Concretely, the influences of microorganisms result in the degradation of the quality of permeates, the reduction in the amount of permeates, the increase in running pressure or in the increase in pressure loss. In order to evade such serious problems, various techniques and methods for bacteriostasis and even disinfecting microbes in membrane separation units have heretofore been proposed. For example, microbicides are used. Most generally, a chlorine-containing microbicide, of which the effect has been verified and which has the advantages of low cost and easy handlability, is added to membrane separation units at a concentration of from 0.1 to 50 ppm or so. One general method of using such a microbicide comprises adding a microbicide to a pre-treatment zone in a membrane separation apparatus, in which the pre-treated water having been subjected to disinfection with sodium hypochlorite and then to flocculation and filtration is, before being fed into the membrane separation units, once stored in a tank, and then processed for removing free chlorine from it through reduction with sodium bisulfite before the safety filter as disposed in the zone before the membrane treatment units.

Chlorine-containing microbicides chemically degrade reverse osmosis membranes. Therefore, when they are used, free chlorine from them must be reduced with a reducing agent before they reach reverse osmosis membranes. As the reducing agent, generally used is sodium bisulfite in an amount of from 1 to 10-fold equivalents. The concentration of the reducing agent is determined in consideration of its ability to completely remove the remaining microbicide and of the probability of its reacting with dissolved oxygen in the system being treated. However, even when a membrane separation apparatus is run in a continuous running manner according to that method of using such a chlorine-containing microbicide, its membrane capabilities are often still worsened, and it has been found that the method is not always satisfactory for disinfecting microorganisms in the apparatus. In this connection, it is said that the chlorine as added in the method oxidizes the organic carbons existing in the crude water being treated, whereby the thus-oxidized organic carbons are converted into compounds that are readily decomposed by microorganisms (see A. B. Hamida and I. Moch, Jr., Desalination & Water Reuse, 6/3, 40–45, 1996), but their theory has not been verified as yet. Given that situation, another method for membrane disinfection has been developed, which comprises intermittently adding sodium bisulfite to a membrane separation system generally at a concentration of 500 ppm. This method has become used in practice, but, in some cases, it is not still effective. Those having tried the method have often experienced deposition of microorganisms on permselective membranes.

OBJECT OF THE INVENTION

In the conventional pre-treatment method, the pre-treated water having been subjected to disinfection and to flocculation and filtration is stored in a tank for a while, which, therefore, is often contaminated with some external contaminants whereby microorganisms much grow in the thus-contaminated, stagnant water to further worsen the quality of the water. The disinfecting effect of sodium bisulfite to be used in the method is for removing oxygen from the crude water being processed and to lower the pH value of the crude water. However, while a permselective membrane apparatus is run according to the method, the intermittent addition of sodium bisulfite to the apparatus is not all the time effective for disinfecting the membrane in the apparatus. We, the present inventors have studied the reason, and have found that ordinary aerobic bacteria that grow in a neutral or alkaline condition could be prevented from growing in an anaerobic environment in some degree but could not be killed in that environment. Having noted it, we have reached the conclusion that the pH depression in the system where bacteria may live is rather the most effective for disinfecting the bacteria therein. That our conclusion is not contradictory to the microbiological viewpoint in this respect. On the other hand, we have further found that, even when a high concentration of sodium bisulfite of 500 ppm is added to crude water having a high salt concentration such as seawater, the pH value of the water system could not be lowered to such a degree that ordinary bacteria existing therein could be killed. Therefore, it is understood that sodium bisulfite added to crude water having a lower salt concentration could exhibit its disinfecting effect not in an anaerobic condition but rather in a lowered pH condition. Accordingly, we have found that adding a high concentration of expensive sodium bisulfite to membrane separation units is not needed for disinfecting them but merely adding inexpensive sulfuric acid or the like thereto to lower the pH value in the system around them is satisfactory for disinfecting the units, and that, when the pre-treated water is prevented from standing for a while in a tank or the like in a water treatment apparatus, then the growth of microorganisms in the apparatus could be inhibited. On the basis of these findings, we have completed the present invention.

DISCLOSURE OF THE INVENTION

The object of the invention can be attained by the constitution mentioned below. Specifically, the invention provides "a method of bacteriostasis or disinfection for a permselective membrane in a membrane separation apparatus for water purification, which comprises a step of treating crude water with an acid at a pH of at most 4", and also provides a method for purifying water that essentially comprises the disinfection method, and an apparatus for the method.

Figure 1:
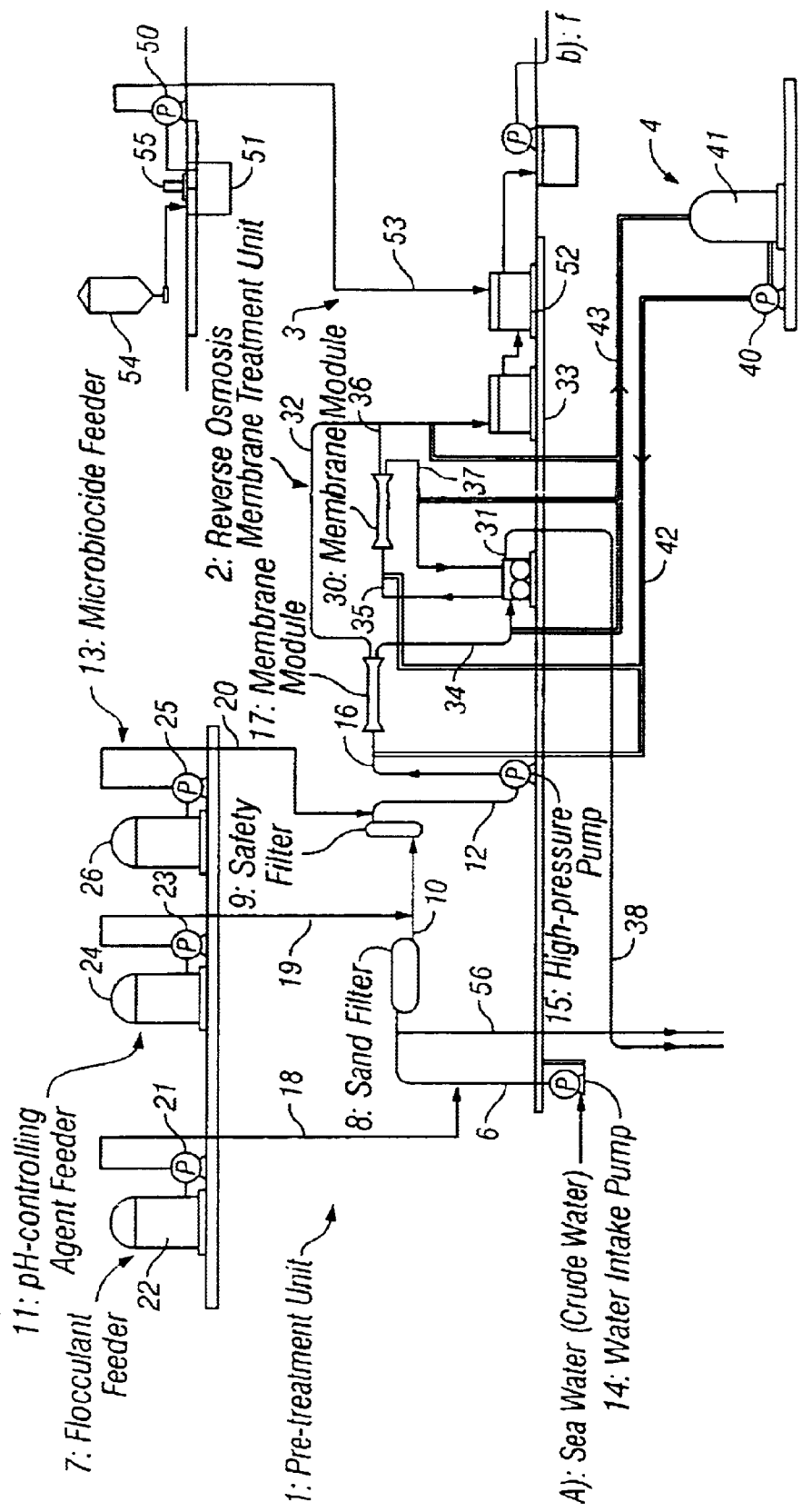
FIG. 1 is a flow chart showing the constitution of the essential parts of a seawater desalination apparatus.

1: pre-treatment unit
2: reverse osmosis membrane treatment unit
3: post-treatment unit
4: membrane washing unit
6: first duct
7: flocculant feeder
8: sand filter (primary filter)
9: safety filter
10: second duct
11: pH controlling agent feeder
12: third duct
13: microbicide feeder

BEST MODE FOR CARRYING OUT THE INVENTION

The membrane separation unit for the invention is one for water production, concentration, separation or the like, in crude water to be treated is fed into a membrane module under pressure and separated into a permeate and a concentrate via the membrane. The membrane module includes a reverse osmosis membrane module, an ultrafiltration membrane module, a precision filtration membrane module, etc. Depending on the type of the membrane module to be used therein, the membrane separation unit is grouped into a reverse osmosis membrane unit, an ultrafiltration membrane unit, and a precision filtration membrane unit. Concretely mentioned herein is a reverse osmosis membrane unit.

The reverse osmosis membrane is a semi-permeable membrane through which a mixed liquid to be separated partly passes therethrough, for example, a solvent of the liquid could pass through it but the other components constituting the liquid could not. A nanofiltration membrane and a loose RO membrane are also within the scope of a broad meaning of the reverse osmosis membrane. Polymer materials of cellulose acetate polymers, polyamides, polyesters, polyimides, vinyl polymers and the like are well used for the reverse osmosis membrane. Depending on its structure, the membrane is grouped into an asymmetric membrane having a dense layer on at least one surface, in which the pore size gradually increases from the dense layer toward the inside of the membrane or toward the opposite surface thereof, and a composite membrane having an extremely thin active layer of a different material formed on the dense layer of the asymmetric membrane. Depending on its shape, the membrane is grouped into a hollow fiber membrane and a flat sheet membrane. The thickness of the hollow fiber membrane and the flat sheet membrane may fall between 10 $\mu$m and 1 mm; and the outer diameter of the hollow fiber membrane may fall between 50 $\mu$m and 4 mm. The asymmetric or composite, flat sheet membrane is preferably supported with a substrate of woven fabric, knitted fabric, non-woven fabric or the like. The disinfection method of the invention in which is used a mineral acid is effectively applicable to any and every type of reverse osmosis membranes, not depending on the material, the structure and the form of the membranes. Typical reverse osmosis membranes to which the invention is applied are, for example, asymmetric membranes of cellulose acetate or polyamide and composite membranes having an active layer of polyamide or polyurea. Of those, the method of the invention is especially effective for asymmetric membranes of cellulose acetate and composite membranes of polyamide, and is more effective for composite membranes of aromatic polyamide (see JP-A 62-121603, 8-138653, U.S. Pat. No. 4,277,344).

The reverse osmosis membrane module is of a practicable form of any of the reverse osmosis membranes noted above, for which a flat sheet membrane is combined with a spiral, tubular or plate-and-frame module, and hollow fiber membranes are bundled up and combined with it. However, the Invention does not depend on the form of the reverse osmosis membrane module.

Regarding its capabilities, the reverse osmosis membrane module for use in the invention has a desalination rate of from 98% to 99.9% and a water production rate of from 10 to 25 $m^3$/day in a standardized size of 1 m (in length)×20 cm (in diameter), when evaluated for crude seawater having a salt concentration of 3.5% (this is the most general seawater concentration) as applied thereto under a pressure of 5.5 MPa and at a temperature of 25° C. for a recovery of 12%; or has a desalination rate of from 98% to 99.9% and a water production rate of from 10 to 25 $m^3$/day in a standardized size of 1 m (in length)×20 cm (in diameter), when evaluated for crude seawater having a salt concentration of 5.8% as applied thereto under a pressure of 8.8 MPa and at a temperature of 25° C. for a recovery of 12%. Preferably, it has a desalination rate of from 99% to 99.9% and a water production rate of from 12 to 23 $m^3$/day in a standardized size of 1 m (in length)×20 cm (in diameter), when evaluated for crude seawater having a salt concentration of 3.5% as applied thereto under a pressure of 5.5 MPa and at a temperature of 25° C. for a recovery of 12%; or has a desalination rate of from 99% to 99.9% and a water production rate of from 12 to 23 $m^3$/day in a standardized size of 1 m (in length)×20 cm (in diameter), when evaluated for crude seawater having a salt concentration of 5.8% as applied thereto under a pressure of 8.8 MPa and at a temperature of 25° C. for a recovery of 12%. More preferably, it has a desalination rate of from 99.3% to 99.9% and a water production rate of from 14 to 20 $m^3$/day in a standardized size of 1 m (in length)×20 cm (in diameter), when evaluated for crude seawater having a salt concentration of 3.5% as applied thereto under a pressure of 5.5 MPa and at a temperature of 25° C. for a recovery of 12%; or has a desalination rate of from 99.3% to 99.9% and a water production rate of from 14 to 20 $m^3$/day in a standardized size of 1 m (in length)×20 cm (in diameter), when evaluated for crude seawater having a salt concentration of 5.8% as applied thereto under a pressure of 8.8 MPa and at a temperature of 25° C. for a recovery of 12%. The reverse osmosis membrane module having a spiral form comprises other members of a water-feeding duct, a permeate-taking out duct and others, in which the other members may be made of any materials. Especially preferably, the module is at least partly so designed that it is applicable to high-concentration crude water having a salt concentration of at least 3.5% and is applicable to high-pressure operation at a pressure of at least 7.0 MPa (see JP-A 9-141060, 9-141067).

The running pressure to be applied to the reverse osmosis membrane unit for use in the invention may fall between 0.1 MPa and 15 MPa, and may vary depending on the type of the crude water to be treated in the unit and on the unit running mode. For example, crude water having a low osmotic pressure, such as saltwater, ultrapure water or the like may be applied to the unit under a relatively low pressure. However, for desalination of seawater, for treatment of drainage and for recovery of useful substances, the crude water to be treated is applied to the unit under a relatively high pressure.

The temperature at which the reverse osmosis membrane unit is run may fall between 0° C. and 100° C. If it is lower than 0° C., the crude water being treated will be frozen so that the unit could not be run; but if higher than 100° C., the crude water applied to the unit will vaporize and could not be well treated.

The recovery in the separation unit may be suitably determined within a range of from 5 to 100%, depending on the mode of running the unit for separation and on the type of the unit. The recovery in the reverse osmosis membrane unit may be suitably determined within a range of from 5 to 98%. For this, however, the pre-treatment condition and the unit running pressure must be taken into consideration, depending on the properties of the crude water to be treated and the concentrate from it, on their concentrations, and even on the osmotic pressure in the unit (see JP-A 8-108048. For example, for seawater desalination, the recovery in the unit having an ordinary efficiency may fall between 10 and 40%, but that in the unit having a high efficiency may fall between 40 and 70%. For saltwater desalination or for ultrapure water production, the unit may be driven to attain a recovery of at least 70%, for example, from 90 to 95%.

Regarding its configuration, the reverse osmosis membrane module may be disposed in a single stage, but if desired, plural reverse osmosis membrane modules may be disposed in series or in parallel relative to the running direction of the crude water to be treated therewith. It is desirable to dispose plural reverse osmosis membrane modules in series relative to the running direction of the crude water to be treated therewith, as the crude water could be contacted with the membrane modules for a long period of time. In that condition, the method of the invention produces better results. Where plural membrane modules are disposed in series relative to the crude water running therethrough, the pressure to the crude water may be suitably increased between the adjacent stages of the modules. The pressure increase may be effected within a range of from 0.1 to 10 MPa, for which a pressure pump or a booster pump may be used. In addition, plural reverse osmosis memorane modules may also be disposed in series relative to the running direction of the permeate passing through them. This method is favorable when the quality of the permeate is desired to be improved further or when the solute in the permeate is desired to be recovered. Where plural reverse osmosis membrane modules are connected in series relative to the permeate passing through them, a pump may be disposed between the adjacent membrane modules via which the pressure to the permeate may be increased, or the permeate having been excessively pressurized in the previous stage may be subjected to the next membrane separation under back pressure thereto. In that condition where plural reverse osmosis membrane modules are connected in series relative to the permeate passing through them, an acid feeder is disposed between the adjacent membrane modules so that the membrane module in the latter stage could be disinfected with an acid from it.

The fraction of the crude water not having passed through the reverse osmosis membrane unit is taken out of the membrane module, and this is a concentrate from the crude water. Depending on its use, the concentrate is further treated and its waste is discarded, or may be again concentrated in any desired method. A part or all of the concentrate may be circulated to and combined with the crude water being treated in the unit. Also depending on its use, the fraction of the crude water having passed through the membrane may be discarded as it is, or may be directly used as it is, or a part or all of the fraction may be circulated to and combined with the crude water being treated in the unit.

In general, the concentrate formed in the reverse osmosis membrane unit has pressure energy, and it is desirable to recover the energy for reducing the unit running cost. For this, an energy recovery unit may be fitted to a high-pressure pump as disposed in any stage, via which the pressure energy of the concentrate could be recovered. Preferably, a specific, turbine-type energy recovery unit is disposed before or after the high-pressure pump or between the adjacent modules, via which the pressure energy of the concentrate could be recovered. Regarding its capabilities, the membrane separation unit could treat water at a rate of from 0.5 $m^3$/day to 1,000,000 $m^3$/day.

In the invention, the crude water to be treated shall have a pH value of at most 4, and the pH control is extremely important for surely disinfecting the permselective membranes used. In particular, when crude seawater is treated through membrane filtration, the effect of the invention is remarkable. The pH value at which microorganisms shall die is specific to the type of microorganisms. For example, the lowermost limit of the pH value at which *Escherichia coli* could grow is 4.6, but *Escherichia coil* shall die at a pH of 3.4 or lower. On the other hand, many types and varieties of microorganisms exist in seawater, and they shall die at different pH values. However, in the invention, when seawater containing such many types and varieties of living microorganisms is kept at a pH of at most 4 for a predetermined period of time, from 50 to 100% of those microorganisms could be killed. For this, preferred is an acidity of pH of at most 3.9, and more preferred is an acidity of pH of at most 3.7. In seawater containing many types and varieties of living microorganisms, some of those microorganisms will be resistant to acids. Even in that case, at least 98% of microorganisms therein could be killed when seawater is kept at a pH of 2.6 or lower for a predetermined period of time. Therefore, the method of the invention could generally produce better results when the crude water to be treated therein is kept at a pH of at most 4 for a predetermined period of time and is occasionally kept at a pH of 2.6 or lower. For the desired pH control in the method, generally employed is an acid. The acid may be any of organic acids and inorganic acids. From the economical aspect, however, sulfuric acid is preferred. The amount of sulfuric acid to be added is proportional to the salt concentration in the crude water to be treated. For example, adding 50 ppm of sulfuric acid to a physiological saline solution (having a salt concentration of 0.9%), which was subjected to pressure disinfection (at 120° C. for 15 minutes), could lower the pH of the solution to 3.2. However, adding even 100 ppm of sulfuric acid to each of three samples of seawater collected in different places and one sample of commercially-available artificial seawater (having a salt concentration of 3.5%), which were all subjected to pressure disinfection (at 120° C. for 15 minutes), lowered the pH of those seawater samples only to the range between 5.0 and 5.8. This will be probably because the pH of those seawater samples would greatly vary essentially depending on the M alkalinity of the seawater. To further lower the pH of those seawater samples, adding at least 120 ppm of sulfuric acid thereto is needed for attaining pH of 4 or lower, or adding at least 250 ppm of sulfuric acid thereto is needed for attaining pH of 2.6 or lower. In consideration of the economical aspect and of the influence on the equipment including pipe lines, the amount of the acid to be added will be preferably 400 ppm, more preferably 300 ppm. Further increasing the concentration of sulfuric acid added to the samples of seawater and artificial seawater noted above to 150 ppm, 200 ppm, 250 ppm and 300 ppm resulted in the reduction in the pH change in the samples of from pH 3.2 to 3.6, from pH 2.8 to 2.9, pH 2.6, and pH 2.4, respectively, in accordance with the increase in the concentration of the acid added. If the pH of seawater to be treated is all the time kept at 2.6, all bacteria including acid-resistant bacteria in seawater will be almost completely killed. However, the proportion of acid-resistant bacteria in seawater is small. Therefore, in the method of the invention, it is desirable that seawater is disinfected generally at a pH of from 2.7 to 4, but occasionally at a pH of 2.6 or lower for disinfecting acid-resistant bacteria therein, for saving the costs of the chemicals to be used and for reducing the influences of the chemicals used on the pipe lines.

For disinfecting the membranes in the method of the invention, an acid may be intermittently added to the crude water after the crude water has been pre-treated and before it is applied to the membrane module. Where plural membrane modules are disposed in series relative to the running direction of the permeate passing therethrough, an acid for membrane disinfection may be intermittently added to the site between the adjacent membrane modules so as to disinfect the latter membrane module. The time for the acid addition and the frequency of the acid addition shall greatly vary, depending on the site to which the acid is added and the condition for the acid addition. For example, the acid addition may be effected over a period of from 0.5 to 2.5 hours, once a day, a week or a month. The same shall apply also to the case of disinfecting acid-resistant bacteria. However, when the acid addition is directed to attaining two different pH conditions in two steps, it is desirable that the step of acid treatment for a pH range of from 2.7 to 4 (step A) is effected at a frequency of once in a period of from one day to 30 days and the step of acid treatment for a pH range of at most 2.6 (step B) is effected at a frequency of once in a period of from 2 days to 180 days. When the step A and the step B are effected plural times within a predetermined period of time, it is desirable that the ratio of the total time for the step A (TA) to that for the step B (TB), TA/TB, falls between 1/100 and 100/1. In consideration of the process cost and the apparatus durability, it is more desirable that the ratio TA/TB falls between 1 and 100. The operation for the step A may be directly switched to that for the step B, and vice versa. However, it is desirable that crude water not subjected to pH control or crude water having a pH of from 6.5 to 7.5 is fed to the system between the step A and the step B. The crude water not subjected to pH control or that having a pH of from 6.5 to 7.5 in this case may be treated in ordinary membrane separation and the resulting permeate or concentrate may be used for its intrinsic purposes. The amount of the additional crude water may vary, depending on the decrease in the amount of the permeate, on the increase in the number of living bacteria in the concentrate and in the organic carbon content of the concentrate, and on the increase in the membrane pressure. Where the membrane separation method of the invention is carried out in a discontinuous manner, the membranes may be dipped in an acid for disinfecting them while the apparatus is stopped.

The disinfection method of the invention may be combined with any other disinfection with chlorine or the like.

The membrane disinfection method of the invention is applicable not only to membrane separation units but also to water separation systems partly comprising membrane separation units.

For example, the invention is applicable to the constitution of the following systems.

A. Water-intake apparatus.
   This is an apparatus for taking crude water, and generally comprises water-intake pumps, chemical feeders, etc.

B. Pre-treatment apparatus connected with water-intake apparatus:
   This is an apparatus for pre-treating crude water to be fed to a permselective membrane apparatus, in which the crude water is purified to a predetermined degree and which comprises, for example, the following units as connected in that order.
   B-1: Flocculation and filtration unit.
   B-2: Polishing filtration unit.
      In place of B-1 and B-2, an ultrafiltration unit or a precision filtration unit may be used.
   B-3: Chemical feeders for feeding flocculants, microbicides, pH controlling agents, etc.

C: Optional intermediate tank connected with pre-treatment apparatus:
   This is for controlling the water level and for buffering the quality of water.

D: Filter connected with the intermediate tank C, or directly with pre-treatment apparatus in the absence of the intermediate tank C:
   This is to remove solid impurities from water to be fed into the membrane separation apparatus.

E. Membrane separation apparatus:
   This comprises high-pressure pumps and permselective membrane modules. In this, plural membrane separation units may be disposed in series or in parallel. Where they are connected in series, a pump may be disposed between the adjacent membrane separation units, via which the water pressure to be applied to the latter unit may be increased.

F. Post-treatment apparatus connected with membrane separation apparatus at the outlet through which the permeate runs out. For example, this comprises any of the following units.
   F-1: Degassing unit, which is for decarbonation.
   F-2: Calcium tower.
   F-3: Chlorine feeder.

G. Post-treatment apparatus connected with membrane separation apparatus at the outlet through which crude water runs out. For example, this comprises any of the following units.
   G-1: Unit for treating crude water having pH of 4, for example, neutralization unit.
   G-2: Drainage.

H. Any other optional apparatus for treating waste water.
   In these systems, pumps may be disposed in any desired zone.

It is desirable that chemicals or chemical solutions for making crude water have a pH of at most 4 are added to the systems in the water intake apparatus A or in the pre-treatment apparatus B, or before the pre-treatment apparatus B, or before the filter D, or after the filter D.

For further enhancing the effect of the invention, it is desirable that the acid feeder is automatically controllable. For example, the acid feeder is preferably equipped with a pump capable of controlling the amount of the acid to be fed. For controlling the acid amount, it is also desirable to dispose a pH meter for measuring the pH of the crude water and the concentrate in any desired site of the system. For controlling the intermittent acid addition, it is still desirable to dispose a timer in the system. Further preferably, the system is equipped with an automatic controller for ensuring automatic running of the system.

The members constituting the apparatus of the invention, such as pipes, valves and others are preferably made of materials that will be not degraded at a pH of 4 or lower. For example, usable are stainless steel members, inner surface-coated members, resin members, etc.

Controlling the pH of crude water to be at most 4 ensures good disinfection of permselective membranes, and, in addition, the thus-controlled crude water is further effective for removing scale in pipe lines. Sodium bisulfite will have to be added for preventing permselective membranes from being degraded by chlorine oxides and the like, and its amount will have to be increased when the microorganisms (including sulfur bacteria, etc.) having adhered onto the membranes increase or when metal salts also having adhered thereonto increase. However, in the invention where the crude water to be treated is acidified, the amount of sodium bisulfite to be added in that condition could be significantly reduced.

The method of the invention is favorable to membrane separation, especially to that of aqueous solutions. In particular, it is especially effective for liquid-solid separation and liquid concentration with precision filtration membranes, for impurity separation and permeate concentration with ultrafiltration membranes, and for solute separation and permeate concentration with reverse osmosis membranes. More specifically, the invention is effective for desalination of seawater, desalination of saltwater, production of industrial water, production of ultrapure water and pure water, production of medical water, concentration of food and drink, purification of city water, quality improvement in city water. In addition, for separating and concentrating organic substances that are readily degraded with conventional oxidizing microbicides, the method of the invention is effective. According to the method of the invention, such organic substances are not degraded through oxidation, and could be surely concentrated and recovered. In producing water to drink in the invention, trihalomethanes that may be formed in disinfection with chlorine are not formed.

For disinfection of crude water in pre-treatment, in general, a chlorine-containing microbicide is continuously added to it, as so mentioned hereinabove. According to the method of the invention, crude water is almost completely disinfected so far as acid-resistant bacteria do not grow in it. Since the microbicide chemically degrades reverse osmosis membranes, a reducing agent such as typically sodium bisulfite is added to crude water before the membrane separation unit. However, in the crude water from which the remaining microbicide is removed in the pre-treatment step, microorganisms could easily grow. In addition, it has been clarified that crude seawater to which no microbicide is added contain specific groups of microorganisms from among many types and varieties of microorganisms, and some of those microorganisms existing in the non-disinfected, crude seawater are acid-resistant ones. Further, it has also been clarified that, when a satisfactory amount of a reducing agent such as typically sodium bisulfite is not added to crude water to which a chlorine-containing microbicide has been added, the microbicide remaining in the crude water could not be completely removed from it, but if the reducing agent is added too much, some types of microorganisms will rather grow in the crude water. For these reasons, it is desirable not to add a chlorine-containing microbicide to the crude water to be treated according to the method of the invention. If so, however, microorganisms will grow in the crude water in the pre-treatment step. The problem could be solved by intermittently adding a microbicide and a reducing agent to crude water. In that condition, the microorganisms having adhered to and deposited on the inner walls of pipes and filtration tanks in the pre-treatment step in the absence of a microbicide could be killed by the microbicide intermittently added thereto. The intermittent addition mode is preferable, as not degrading the membranes. The interval for the intermittent microbicide addition may be determined depending on the quality of the crude seawater to be treated and on the condition of the microorganisms growing therein. For example, a microbicide may be added once at intervals of from 1 day to 6 months, and the time for the addition may be from 30 minutes to 2 hours or so. Depending on the interval, the membranes may be disinfected according to the method of the invention. The intermittent, chlorine-containing microbicide addition significantly reduces the treatment cost, which is ensured for the first time only by the membrane disinfection method of the invention but not at all by the conventional membrane disinfection method of using a high concentration of sodium bisulfite. This is because the conventional membrane disinfection method is not satisfactory for completely disinfecting microorganisms. For preventing the adhesion and deposition of microorganisms in the absence of a microbicide, and for enhancing the disinfection effect of the invention, one favorable system is mentioned below, as illustrated in FIG. 1.

The system of FIG. 1 is for desalination of seawater, which comprises a pre-treatment unit 1, a reverse osmosis unit 2, a post-treatment unit 3, and a membrane washer unit 4. The pre-treatment unit 1 comprises a flocculant feeder 7 through which a flocculant solution is added to the seawater (crude water) running through the first duct 6; a sand filter 8 which is a primary filter means; a safety filter 9 which is a secondary filter means; a pH-controlling agent feeder 7 through which a pH-controlling mineral acid solution is added to the primary filtrate running through the second duct 10; and a microbicide feeder 13 through which a microbicide solution is added to the secondary filtrate running through the third duct 12.

The first duct 6 is connected with the water intake pump 14 and with the sand filter 8; the second duct 10 is connected with the sand filter 8 and with the safety filter 9; the third duct 12 is connected with the high-pressure pump 15 and with the first-stage membrane module 17 in the reverse osmosis unit 2.

Accordingly, seawater can be fed to the sand filter 8 by driving the water intake pump 14, and the secondary filtrate can be pressurized to a high degree and fed to the reverse osmosis membrane unit 2 by driving the high-pressure pump 15. In this step, ferric chloride having a predetermined concentration is added to the seawater through the flocculant feeder 7 via the duct 18, while sulfuric acid is added thereto through the pH-controlling agent feeder 11 via the duct 19; and a sulfuric acid solution is intermittently added thereto through the microbicide feeder 13 via the duct 20. The duct 20 may be connected with the duct 12, or, as the case may be, the pH-controlling agent feeder 11 and the microbicide feeder 13 can be integrated into one unit.

From the tank 22 of the flocculant feeder 7, a ferric chloride solution is fed into the crude seawater being treated, by driving the pump 21; and from the tank 24 of the pH-controlling agent feeder 11, sulfuric acid is fed into the crude seawater by driving the pump 23.

In the system of FIG. 1, the pipe line from the water intake pump 14 to the first-stage membrane module 17 in the reverse osmosis membrane unit 2 is a closed pipe line. In other words, this is not a so-called open pipe line where the crude water being treated is temporarily stored in a tank, as in a conventional system, but is a non-open, closed pipe line. The system of the invention may comprise a crude water tank, a sand filtration tank and a feeding pump, in which, however, the pipe line from the water intake unit to the reverse osmosis membrane module is preferably a non-open, closed pipe line.

In the non-open, closed pipe line, the crude water being treated is protected from being contaminated with any external contaminants, and can be treated continuously. The flow rate change after the high-pressure pump 15 may be prevented by controlling the flow rate in the units constituting the pre-treatment unit 1. In that condition, the crude water can be kept all the time flowing through the pipe line, not standing anywhere in the pipe line, and can be treated continuously in the line. The sand filter 8 can be driven always stably.

In the pre-treatment unit, a polishing filter may be disposed after the sand filter. If desired, a UF or MF membrane having a pore size of from 0.01 to 1.0 μm may be used in place of the sand filter or the polishing filter or in place of the two.

In the system illustrated, the crude water being treated does not stay in a tank or the like, and therefore adhesion and deposition of microorganisms in the pipe line even in the absence of a microbicide therein can be prevented. Therefore, the disinfecting effect of the invention can be enhanced in the system of that type.

EXAMPLES

The invention is described concretely with reference to the following Examples, which, however, are not intended to restrict the scope of the invention. In these Examples, the disinfecting effect is represented by the number of living microorganisms, the pressure loss in membrane modules and the consumption of sodium bisulfite (SBS).

Reference Example 1

A predetermined amount of a suspension of living cells of *Escherichia coli* K12 IFO 3301 was added to a physiological saline solution (having a salt cuncentration of 0.9%) that had been subjected to pressure disinfection (at 120° C. for 15 minutes) and then to pH control with sulfuric acid added thereto, and kept at 20° C. for a predetermined period of time, and the survival rate of the cells was obtained by dividing the number of the living cells still remaining in the solution by the number of the cells added to the solution. As a result, the survival rate of the cells was not lower than 90% when the solution to which had been added 10 ppm of sulfuric acid and which had a pH of 4.7 was kept under the condition for 2.5 hours. However, the survival rate of the cells in the solution having a pH of 3.2, to which had been added 50 ppm of sulfuric acid, was 90% after kept for 0.5 hours, 20% after kept for 1 hour, and 1% or lower after kept for 2.5 hours. When 100 ppm of sulfuric acid was added to the solution, the survival rate of the cells in the solution was 1% or lower after 0.5 hours.

Reference Example 2

To a commercially-available, 3.5% artificial seawater that had been subjected to pressure disinfection (at 120° C. for 15 minutes) and then to pH control with sulfuric acid added thereto, added was a predetermined amount of the same suspension of *Escherichia coli* cells as in Example 1, or a predetermined amount of a suspension of a solid deposit on a reverse osmosis membrane having been used in seawater desalination, or a predetermined amount of un-identified bacteria as separated from the solid deposit suspension, of which the number was the largest among all bacteria separated from the suspension. Then, each seawater was kept as such at 20° C. for a predetermined period of time, and the survival rate of the cells therein was measured. The data are shown in Table 1. For comparison, 500 ppm of sodium bisulfite was added in place of sulfuric acid, and the data obtained are also shown in Table 1. From the data in Table 1, it is understood that the cells in the seawater were killed to an extremely high degree when the seawater was kept at a pH of 4.0 or lower for a period of 0.5 hours or longer.

TABLE 1

| | | | | | Survival Rate (%) | | |
|---|---|---|---|---|---|---|---|
| Additive | Concentration (ppm) | Time (hr) | pH | *E. coli* | Suspension of Deposit on Membrane | Cells from Deposit on Membrane |
| None | — | 2.5 | 8.5 | 100 | 100 | 100 |
| Sodium Bisulfite | 500 | 2.5 | 5.9 | 98 | 90 | 86 |
| Sulfuric Acid | 100 | 2.5 | 5.1 | 107 | 60 | 81 |
| Sulfuric Acid | 120 | 0.5 | 4.0 | 105 | 37 | |
| Sulfuric Acid | 120 | 2.5 | 4.0 | 93 | 15 | |
| Sulfuric Acid | 150 | 0.5 | 3.3 | <1 | <1 | <1 |
| Sulfuric Acid | 200 | 0.5 | 2.9 | <1 | <1 | <1 |
| Sulfuric Acid | 300 | 0.5 | 2.5 | <1 | <1 | <1 |

Example 1

Two membrane separation units each having a reverse osmosis membrane of polyamide were driven for seawater desalination through reverse osmosis filtration to produce fresh water. To one of the two units, crude seawater having been pre-treated and subjected to pH control to have a pH of from 3.5 to 4.0 with sulfuric acid added thereto was applied everyday for a period of 30 minutes a day. In that condition, the two units were continuously driven for 1 month. As a result, the pressure loss in the unit to which no sulfuric acid had been added increased, but the pressure loss in the other unit to which sulfuric acid had been added did not change. While the units were driven under the condition, the number of the living cells in the concentrate having passed through each unit was counted. As a result, the number of the living cells in the concentrate in the unit that had been subjected to the sulfuric acid treatment was lowered to 1/100 or less, as compared with that of the living cells in the concentrate in the other unit not subjected to the sulfuric acid treatment.

Example 2

Crude seawater, in which the number of the living cells was 200 cells/ml as counted with an agar plate counter, was applied to a membrane separation unit having a reverse osmosis membrane of polyamide, in which the crude seawater was subjected to reverse osmosis separation. In the pre-treatment unit before the membrane separation unit, a chlorine-containing microbicide was continuously added to the crude seawater so that the remaining chlorine concentration therein could be 1 ppm. Just before the reverse osmosis membrane module in the separation unit, sodium bisulfite was added to the crude seawater being treated. The amount of sodium bisulfite added was so controlled that the remaining sodium bisulfite concentration in the brine to be taken away through the module could be at least 1 ppm. The consumption of sodium bisulfite was 5 ppm in the initial stage. However, after the system was continuously driven for 10 days, the consumption of sodium bisulfite increased up to 35 ppm. Within those 10 days, the pressure loss in the membrane module increased by about 0.01 MPa.

Next, crude seawater having been subjected to pH control to have a pH of from 3 to 4 with sulfuric acid added thereto was passed through the membrane separation unit for a period of 30 minutes a day. As a result, the consumption of sodium bisulfite decreased to 8 ppm. In this case, the pressure loss increased by 0.01 MPa, as compared with the original value, and was kept later as such.

Example 3

Crude seawater, in which the number of the living cells was 200,000 cells/ml as counted with an agar plate counter, was applied to a membrane separation unit having a reverse osmosis membrane of polyamide, in which the crude seawater was subjected to reverse osmosis separation. In the pre-treatment unit before the membrane separation unit, a chlorine-containing microbicide was continuously added to the crude seawater so that the remaining chlorine concentration therein could be at least 1 ppm, and 6 ppm of a de-chlorinating agent of sodium bisulfite was also continuously added thereto. In the membrane separation unit, 500 ppm of sodium bisulfite was added to the crude seawater over a period of 1 hour a week. After the system was driven for about 1 month, the pressure loss in the membrane separation unit increased by about 0.02 MPa, as compared with the initial value.

The same crude seawater was treated in the same system as above. In this case, however, 1 ppm of the chlorine-containing microbicide was intermittently added to the crude seawater in the pre-treatment unit over a period of 1 hour a day, and 6 ppm of sodium bisulfite was thereto over a period of 3 hours a day; and crude seawater having been subjected to pH control to have a pH of 4 with sulfuric acid added thereto was applied to the membrane separation unit over a period of 1 hour a day. After about 1 month, the pressure loss in the membrane separation unit changed little.

Example 4

The same crude seawater was pre-treated in the same manner as in-the latter process of Example 3. Then, the crude seawater was treated in the same membrane separation unit as in Example 3. In this, however, the membrane in the unit was not disinfected, and the system was driven for 50 days. As a result, the pressure loss in the membrane separation unit increased by 0.03 MPa. After this stage, crude seawater having been subjected to pH control to have a pH of 3 with sulfuric acid added thereto was applied to the membrane separation unit, over a period of 1 hour a day. After 8 days, the pressure loss decreased by 0.015 MPa. Next, the system was driven for further 20 days without disinfecting the membrane separation unit. As a result, the pressure loss increased by 0.02 MPa. After this stage, crude seawater having been subjected to pH control to have a pH value of 4 with sulfuric acid added thereto was applied to the membrane separation unit, over a period of 1 hour a day. After 12 days, the pressure loss again decreased by 0.012 MPa.

Example 5

In a system comprising a pre-treatment unit and a membrane separation unit having a module of reverse osmosis membrane of polyamide, crude seawater was desalinated through reverse osmosis filtration into fresh water. In the pre-treatment unit, continuously added was chlorine to the crude seawater so that the remaining chlorine concentration therein could be 1 ppm, and sodium bisulfite was added to the crude seawater before the reverse osmosis membrane module. The amount of sodium bisulfite added was so controlled that the remaining sodium bisulfite concentration in the brine to be taken away from the reverse osmosis membrane module could be at least 1 ppm. After the system was driven, the consumption of sodium bisulfite increased. After 10 days, the consumption of sodium bisulfite (this is obtained by subtracting the amount of sodium bisulfite remaining in the brine from that added to the crude seawater) reached 21 ppm. After this, crude seawater having been subjected to pH control to have a pH of 2.5 with sulfuric acid added thereto was passed through the membrane unit over a period of 30 days on day 1, day 2 and day 10, and crude seawater also having been subjected to pH control to have a pH of 3 with sulfuric acid added thereto was passed therethrough over a period of 30 minutes on day 14 and day 27. In this stage, the consumption of sodium bisulfite decreased to 10 ppm.

TABLE 2

| | | Pre-treatment Disinfection | | RO Disinfection | | |
|---|---|---|---|---|---|---|
| | Number of Living Cells | Microbi-cide*/-Reducing Agent | Time (min/day) | Microbi-cide | Time (min/day) | pH |
| Example 1 | | None | — | Sulfuric Acid | 30 | 3.5 to 4 |
| | | | | None | — | 6.5 |
| Example 2 | 200 | Cl-contain-ing microbi-cide/-NaHSO$_3$ (1 ppm excessive each) | continuous addition | None | — | |
| | | | | Sulfuric Acid | 30 | 3 to 4 |
| Example 3 | 200,000 | Cl-contain-ing microbi-cide/-NaHSO$_3$ (1 ppm excessive/6 ppm) | continuous addition 60/180 | NaHSO$_3$ 500 ppm Sulfuric Acid | 60/7 (60 minutes a week) 60 | 4.0 |
| Example 4 | 200,000 | Cl-contain-ing microbi-cide/-NaHSO$_3$ (1 ppm excessive/6 ppm) | 60/180 | None Sulfuric Acid None Sulfuric Acid | — 60 — 60 | 3.0 4.0 |

TABLE 2-continued

| | | | | | |
|---|---|---|---|---|---|
| Example 5 | Cl-contain-ing microbi-cide/-NaHSO₃ (1 ppm excessive each) | continuous addition | None Sulfuric Acid | — 30 | 2.5 3 |

| | | Results | | |
|---|---|---|---|---|
| | Running Period (days) | Increase in Pressure Loss | Number of Living Cells | NaHSO₃ Consump-tion |
| Example 1 | 1 to 30 | No Yes | Decreased to 1/100 or less | |
| Example 2 | 0 1 to 10 11 to 11 | 0.01 MPa 0.01 MPa | | 5 ppm 35 ppm 8 ppm |
| Example 3 | 1 to 30 1 to 30 | 0.02 MPa No | | |
| Example 4 | 1 to 50 51 to 58 59 to 78 79 to 90 | 0.03 MPa −0.015 MPa 0.020 MPa −0.012 MPa | | |
| Example 5 | 1 to 10 11, 12 & 20th 14, 27th | | | 21 ppm 10 ppm |

*"1 ppm excessive" means that the remaining chlorine concentration in the crude seawater as treated in the pretreatment unit was 1 ppm, and that the reducing agent having remained in the brine as taken away from the reverse osmosis membrane module was 1 ppm.

Comparative Example 1

1% of seawater was added to commercially-available, 3.5% artificial seawater having been subjected to pressure disinfection (at 120° C. for 15 minutes), and the pH of the resulting seawater mixture was measured to be 8.5. After having been kept at 20° C. for 2 hours, 0.1 ml of the seawater mixture was applied onto an agar medium for marine bacteria, of which the pH value had been controlled to be 7, and then kept warmed at 20° C. After incubated for a few days, the medium had 200 colonies formed thereon.

Reference Example 3

1% of seawater was added to commercially-available, 3.5% artificial seawater having been subjected to pressure disinfection (at 120° C. for 15 minutes) and then to pH control with 200 ppm of sulfuric acid added thereto. The pH of the resulting seawater mixture was 2.8. After having been kept at 20° C. for 2 hours, 0.1 ml of the seawater mixture was applied onto an agar medium for marine bacteria, of which the pH value had been controlled to be 7. After incubated for a few days, the medium had 3 colonies formed thereon. The data in this Reference Example 3 are shown in Table 3, along with those in Comparative Example 1. The microbes having formed the colonies on the agar media are acid-resistant microbes that could not be killed at a pH of 2.8, and it is believed that 1.5% of such acid-resistant microbes existed in the seawater tested herein.

TABLE 3

| | Condition for Treatment | Number of Colonies Formed |
|---|---|---|
| Comparative Example 1 | pH 8.5, for 2 hours | 200 |
| Reference Example 3 | pH 2.8, for 2 hours | 3 |

Reference Example 4

To commercially-available 3.5% artificial seawater having been subjected to pressure disinfection (at 120° C. for 15 minutes) and then to pH control with sulfuric acid added thereto, added were a predetermined amount of un-identified acid-resistant bacteria (3 strains in all) that had been obtained in Example 7, and kept at 20° C. for a predetermined period of time. Then, the survival rate of the bacteria in the pH-controlled artificial seawater was obtained, and the data are shown in Table 4. From Table 4, it is understood that the seawater is well disinfected when kept at a pH of 2.6 or lower for a period of 0.5 hours or longer.

TABLE 4

| | | | | Survival Rate (%) | | |
|---|---|---|---|---|---|---|
| Additive | Concentration (ppm) | Time (hr) | pH | Acid-resistant Bacteria 1 | Acid-resistant Bacteria 2 | Acid-resistant Bacteria 3 |
| None | — | 1 | 8.0 | 74 | 89 | 29 |
| Sulfuric Acid | 200 | 1 | 2.8 | 50 | 22 | <1 |
| Sulfuric Acid | 250 | 0.5 | 2.6 | 17 | 33 | 1 |
| Sulfuric Acid | 250 | 1 | 2.6 | <1 | 2 | <1 |
| Sulfuric Acid | 250 | 2.5 | 2.6 | <1 | <1 | <1 |
| Sulfuric Acid | 300 | 0.5 | 2.6 | 8 | 1 | <1 |
| Sulfuric Acid | 300 | 1 | 2.4 | <1 | <1 | <1 |

Example 6

Two membrane separation systems (systems A and B) each comprising a pre-treatment unit and a membrane separation unit having a reverse osmosis membrane module of polyamide were driven for seawater desalination through reverse osmosis filtration to produce fresh water. In these, a culture of the acid-resistant bacteria having been obtained in Reference Example 3 was added to the pre-treated seawater. Seawater having been subjected to pH control to have a pH of from 3.5 to 4.0 was passed through the both systems over a period of 30 minutes a day. These systems thus having been subjected to pH control were more stably driven, as compared with others not subjected to pH control. However, after these systems were continuously driven for 30 days in that condition, the pressure loss in the membrane separation unit increased. After this state, seawater having been subjected to pH control to have a pH of 2.6 was passed through the system A over a period of 30 minutes a day, while seawater having been subjected to pH control to have a pH of from 3.5 to 4.0 was passed through the system B also over a period of 30 minutes a day. Through the system B, seawater having been subjected to pH control to have a pH of 2.6 was additionally passed over a period of 30 minutes a day, but once at intervals of 5 days. In those conditions, the two systems were continuously driven for 30 days. As a result, the pressure loss in the membrane separation unit in the two systems did not change. While the systems were driven under the defined conditions, the number of living cells in the concentrate was counted. The number of living cells in the concentrate in the two systems decreased to 1/100 or less, as compared with that in the concentrate in those systems where only seawater having a controlled pH value of from 3.5 to 4.0 was passed. The data are shown in Table 5. From Table 5, it is understood that the disinfecting effect of the seawater having a controlled pH value of from 3.5 to 4.0 is not so good, but the disinfecting effect of the seawater having a controlled pH value of 2.6 is satisfactory. In addition, it is also understood that the disinfecting effect of the seawater could be satisfactorily enhanced only when the pH value of the seawater is lowered to 2.6 once at intervals of 5 days.

TABLE 6

| Treatment with Acid Water | Ratio of Living Microbes in Concentrate | Ratio of Sulfuric Acid Used |
|---|---|---|
| pH 3.5 to 4.0, 30 minutes a day | 100 | 1 |
| pH 2.6, 30 minutes a day | <1 | 2 |
| pH 3.5 to 4.0, 30 minutes a day pH 2.6, 30 minutes a day (once at intervals of 5 days) | <1 | 1.2 |

INDUSTRIAL APPLICABILITY

For disinfecting microorganisms that exist on and around membranes in a membrane separation apparatus for water purification, the method of the invention is better than conventional methods of intermittently adding high-concentration sodium bisulfite to the apparatus. According to the method of the invention, microorganisms in the apparatus are all surely killed.

What is claimed is:

1. A method of bacteriostasis or disinfection for permselective membranes in a membrane separation apparatus for water purification, which comprises subjecting crude water to acid treatment, while the membrane remains in operation, said acid treatment comprising a first acid treatment at a pH of from about 2.7 to about 4 and a second acid treatment at a pH of about 2.6 or lower.

2. The method of bacteriostasis or disinfection for permselective membranes as claimed in claim 1 where the acid treatment is effected intermittently, and the time for the treatment is between about 0.5 and about 2.5 hours.

3. The method of bacteriostasis or disinfection for permselective membranes as claimed in claim 2 wherein the acid treatment is repeated at intervals of from 1 day to 1 month.

4. The method of bacteriostasis or disinfection for permselective membranes as claimed in claim 1 in which the second acid treatment is repeated at intervals of from 2–180 days.

5. The method of bacteriostasis or disinfection for permselective membranes as claimed in claim 2 wherein the permselective membranes are reverse osmosis membranes.

6. The method of bacteriostasis or disinfection for permselective membranes as claimed in claim 1 wherein the crude water to be treated is seawater.

7. The method of bacteriostasis or disinfection for permselective membranes as claimed in claim 1 wherein the acid treatment includes adding at least 120 ppm of sulfuric acid to the crude water.

8. A method of claim 1, further comprising providing apparatus which comprises a first duct for feeding crude water to a sand filter, a second duct for feeding filtered crude water from the sand filter to a safety filter, a third duct for feeding filtered crude water to a reverse osmosis membrane apparatus, a flocculant feeder for feeding a flocculant to the first duct, a pH-controlling agent feeder for feeding a pH-controlling mineral acid to the second duct, and a microbicide feeder for feeding a microbiocidal mineral acid to any one of the first, second or third duct, for carrying out the acid treatment.

9. The method and separating of purifying water as claimed in claim 8 wherein the crude water is seawater.

10. The method for separating and purifying water as claimed in claim 8 wherein the crude water is subjected to intermittent disinfection with chlorine, prior to the acid treatment.

11. A pre-treatment apparatus for a reverse osmosis membrane treatment apparatus, which comprises a first duct for feeding crude water to a sand filter, a second duct for feeding filtered crude water from the sand filter to a safety filter, a third duct for feeding filtered crude water from said safety filler to a reserve osmosis membrane apparatus means for maintaining continuous flow in the third duct by controlling the flow upstream thereof a flocculant feeder for feeding a flocculant to the first duct, a pH-controlling agent feeder for feeding a pH-controlling mineral acid to the second duct, and a microbiocide feeder for feeding a microbiocidal mineral acid to any one of the first, second or third ducts.

* * * * *